US00PP35655P3

(12) United States Plant Patent
Meilland

(10) Patent No.: US PP35,655 P3
(45) Date of Patent: Feb. 20, 2024

(54) MINIATURE ROSE PLANT NAMED 'MEIZENDO'

(50) Latin Name: *Rosa hybrida*
Varietal Denomination: MEIZENDO

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/215,988

(22) Filed: Jun. 29, 2023

(65) Prior Publication Data

US 2024/0008378 P1 Jan. 4, 2024

(30) Foreign Application Priority Data

Jul. 4, 2022 (QZ) ..... PBR 2022/1657

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121, 123, 128
See application file for complete search history.

(56) References Cited

U.S. PATENT DOCUMENTS

PP17,877 P3 7/2007 Meilland
PP19,032 P2 7/2008 Radler

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIZENDO', is disclosed. The new variety forms attractive, semi-double, dark pink colored flowers. Attractive rather dense, semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*
Variety denomination: 'MEIZENDO'.

CROSS REFERENCE TO RELATED APPLCIATIONS

This application claims priority to Plant Breeders' Right Application Number 2022/1657, which was filed at Community Plant Variety Office in the European Union on Jul. 4, 2022, the contents of which are hereby incorporated by reference for all purposes.

STATEMENT REGARDING PRIOR DISCLOSURES BY THE INVENTOR

The first offer for sale of the new variety was Feb. 20, 2023, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) that is the product of the cross between an unnamed seedling (not patented) and the 'MEITRIDO' variety (not patented). The male parent (i.e., the pollen parent) of the new variety was the 'RADSWEET' variety (U.S. Plant Pat. No. 19,032).

The parentage of the new variety can be summarized as follows:

(Unnamed Seedling x 'MEITRID0') X 'RADSWEET'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms dark pink colored flowers, (b) produces semi-double flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed female parent (i.e., the seed parent) produces double flowers, whereas the new variety produces semi-double flowers. In addition, the 'RADSWEET' variety (i.e., pollen parent) exhibits shrub growth habit and produces light pink colored flowers which are larger sized flowers compared to flowers of the new variety and the new variety exhibits bushy growth habit and produces dark pink colored flowers. Moreover, the new variety can be readily distinguished from other similar non-parental varieties. For example, the 'MEIGALPIO' variety (U.S. Plant Pat. No. 17,877) produces flowers which are more red in color compared to flowers of the new variety.

The new variety has been named 'MEIZENDO'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during June while budded on Rosa Manetti and growing outdoors at Le Cannet des Maures, Var, France. Dimensions in centimeters are indicated at the bottom of the drawing.

Element 1 illustrates a specimen of a young shoot.

Element 2 illustrates a specimen of a floral bud before the opening of the sepals.

Element 3 illustrates a specimen of a floral bud at the opening of the sepals.

Element 4 illustrates a specimen of a floral bud at the opening of the petals.

Element 5 illustrates a specimen of a flower in the course of opening.

Element 6 illustrates a specimen of an open flower — plan view — obverse.

Element 7 illustrates a specimen of an open flower — plan view — reverse.

Element 8 illustrates a specimen of a fully open flower — plan view — obverse.

Element 9 illustrates a specimen of a fully open flower — plan view — reverse.

Element 10 illustrates a specimen of a floral receptacle showing arrangement of the stamens and pistils.

Element 11 illustrates a specimen of a floral receptacle showing arrangement of the pistils (stamens removed).

Element 12 illustrates a specimen of a flowering stem.

Element 13 illustrates a specimen of a leaf with 3 leaflets — plan view — upper surface.

Element 14 illustrates a specimen of a leaf with 3 leaflets — plan view — under surface.

Element 15 illustrates a specimen of a leaf with 5 leaflets — plan view — upper surface.

Element 16 illustrates a specimen of a leaf with 5 leaflets — plan view — under surface.

Element 17 illustrates a specimen of a leaf with 7 leaflets — plan view — upper surface.

Element 18 illustrates a specimen of a leaf with 7 leaflets — plan view — under surface.

Element 19 illustrates specimen of buds in a cluster.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of two-years-old specimens of the new variety during June while budded on Rosa Manetti and growing outdoors at Le Cannet des Maures, Var, France.

Botanical classification: *Rosa hybrida* cultivar MEIZENDO.

Commercial classification: Miniature Rose Plant.

Plant:

*Habit*.—Bushy.

*Height*.—Approximately 40 cm on average.

*Width*.—Approximately 40 cm on average.

Branches:

*Color*.—Young stems: commonly near Green Group 143B. Adult wood: commonly near Green Group 138B.

*Length*.—From the crown to the flower is typically between 20 cm to 30 cm.

*Diameter*.—Typically between 0.2 cm to 0.5 cm.

*Thorns*.—Configuration on adult stems: concave, very elongated and curved downwards on the upper surface and very concave on the under surface. Long prickles — quantity: approximately 10 thorns on average per 10 cm long young stem and approximately 10 thorns on average per 10 cm long adult stem. Long prickles — length: typically between 0.5 cm to 0.8 cm on young stems and typically between 0.5 cm to 0.8 cm on adult stems. Long prickles — width at base: typically between 0.4 cm to 0.8 cm on young stems and typically between 0.4 cm to 0.8 cm on adult stems. Long prickles — base shape: oval, narrow, and medium on young stems and on adult stems. Long prickles — color on young stems: commonly near Yellow-Green Group 144A. Long prickles — color on adult stems: commonly near Greyed-Yellow Group 160A. Small prickles — quantity: absent.

*Internode*.—Numbers on the entire branch: typically 5 or 6 on average. Length: typically between 2 cm to 5 cm.

Foliage:

*General appearance*.—Rather dense, semi-glossy.

*Number of leaflets*.—3, 5, 7; most often 5.

5 *leaflets leaf*.—Length: typically between 9.5 cm to 14.0 cm. Width: typically between 5.5 cm to 7.5 cm.

*Terminal leaflet*.—Length: typically between 3.5 cm to 5.5 cm. Width: typically between 2.0 cm to 3.0 cm.

*Young shoots*.—Anthocyanin coloration: absent.

*New foliage*.—Upper surface color: commonly near Green Group 143A. Under surface color: commonly near Green Group 139C.

*Adult foliage*.—Upper surface color: commonly near Green Group 137A. Under surface color: commonly near Green Group 138B.

Leaflets:

*Shape*.—Tip: acute. Base: rounded.

*Intensity of glossiness*.—Weak.

*Texture*.—Moderately leathery.

*Smoothness*.—Upper and under surfaces are smooth.

*General appearance*.—Lanceloate.

*Serration*.—Small and single.

*Undulation on the margin*.—Very weak.

*Venation*.—Color is commonly near Yellow-Green Group 145A and pattern is imparipinnate.

*Petiole rachis*.—Color of upper surface: commonly near Green Group 137A. Color of under surface: commonly near Yellow-Green Group 144A. Texture: upper surface is glandular, under surface is smooth. Rachis of terminal leaflet: length is typically between 3.0 cm to 4.2 cm and diameter is approximately 0.1 cm on average.

*Petioles*.—Upper surface: smooth. Under surface: smooth. Color of upper surface: commonly near Green Group 137B with a center line near Yellow-Green Group 145C. Color of under surface: commonly near Yellow-Green Group 144A. Length: typically between 2.0 cm to 4.0 cm. Diameter: approximately 0.1 cm on average.

*Stipules*.—Length: approximately 2.0 cm on average. Width: typically between 0.1 cm to 0.2 cm. General appearance: narrow. Texture: smooth on upper and under surfaces. Color of upper surface: commonly near Green Group 137A. Color of under surface: commonly near Green Group 138A.

Inflorescence:

*Number of flowers per stem*.—Typically between 1 to 5 flowers per stem.

*Lastingness of the bloom*.—On the plant: approximately 3 weeks on average. In vase: not tested.

*Bud*.—Shape: ovoid. Size: small. Length: approximately 1.8 cm on average. Width: approximately 1.4 cm on average. Color as calyx breaks: upper surface: commonly near a color between Red Group 50A and near Red Group 52A; basal spot is very little and color is commonly near Yellow Group 3A. under surface: commonly near Red Group 50A; basal spot is very little and color is commonly near Yellow Group 3A.

*Sepals*.—Number: commonly 5. Length: typically between 1.5 cm to 1.7 cm on average. Width: typically between 0.4 cm to 0.6 cm (on median part). Shape: at the top: elongate and narrow. at the base: flat at union with the receptacle. Extensions: typically 2 sepals without extensions, 3 sepals with small extension which length of extension is typically between 0.2 cm to 4.0 cm and width of extension is typically less than 0.1 cm. Upper surface: texture: tomentous. color: commonly near Green Group 138A. Under surface: texture: glandular. color: commonly near Green Group 138A.

*Receptacle*.—Color: commonly near Green Group 138B. Length: approximately 0.6 cm on average. Width: approximately 0.5 cm on average. Surface: smooth. Shape: pitcher shaped.

*Peduncle*.—Length: typically between 3.0 cm to 4.0 cm. Width: typically between 0.1 cm to 0.15 cm. Surface: glandular. Color: commonly near Yellow-Green Group 144A.

*Flower*.—Diameter when open: approximately 4.0 cm on average. Depth of the flower: approximately 1.5 cm on average. Shape: cup shaped. Shape when viewed from above: irregular rounded. Shape of the upper part of the flower profile: cup. Shape of the lower part of the flower profile: quasi flat. Type: semi-double. Number of petals under normal conditions: typically between 7 to 8. Petals: shape: obovate (cuspidate at the top and cuneiform at the base). length: typically between 1.7 cm to 2.1 cm. width: typically between 1.3 cm to 1.9 cm. Undulation of the petal: very weak. Reflexing of the petal: absent. Petal incision: very weak. Petal arrangement: imbricated with 1 or 2 petaloids (petaloids shape is deformed petals). Petal drop: petals drop off cleanly before drying. Fragrance: slight, very sweet. Discoloration of the flower: evolution to near Red-Purple Group 57A. Color when opening: basal spot on the upper surface: commonly near Yellow Group 3A. upper surface: commonly near a color between Red Group 50A and Red Group 52A. basal spot on the under surface: commonly near Yellow Group 3A. under surface: commonly near Red Group 50A. Color of the open flower: basal spot on upper surface: commonly near Yellow Group 3C. upper surface: commonly near a color between Red Group 52A and Red-Purple Group 57B. basal spot on under surface: commonly near Yellow Group 3C. under surface of the flower: commonly near Red Group 52A. Anthers: typically 90 on average, length is approximately 0.1 cm on average, width is approximately 0.1 cm on average, coloration is commonly near Greyed-Orange Group 172A bordered with near Greyed-Orange Group 164A, and arrangement is regular around styles. Filaments: length is typically between 0.2 cm to 0.5 cm and coloration is commonly near Greyed-Orange Group 163B. Styles: length is approximately 0.3 cm on average, coloration is commonly near Greyed-Purple Group 181B, and number is typically approximately 20 on average. Stigmas: length is approximately 0.1 cm on average and coloration is commonly near Greyed-Yellow Group 162A. Pollen: medium quantity; color is commonly near Greyed-Orange Group 163B. Hips: information not available.

Development:

*Vegetation*.—Medium.

*Blooming*.—Exceptional blooming all season long; early in the season, abundant and nearly continuous, typically from May to first frost in France.

*USDA hardiness zone*.—Zone 5 to 9.

*Tolerance to disease*.—Good, and particularly against black spot (*Diplocarpon rosae*).

The new 'MEIZENDO' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIZENDO' characterized by the following combination of characteristics:

(a) forms dark pink colored flowers, (b) produces semi-double flowers, and (c) exhibits a bushy growth habit;

substantially as herein shown and described.

* * * * *

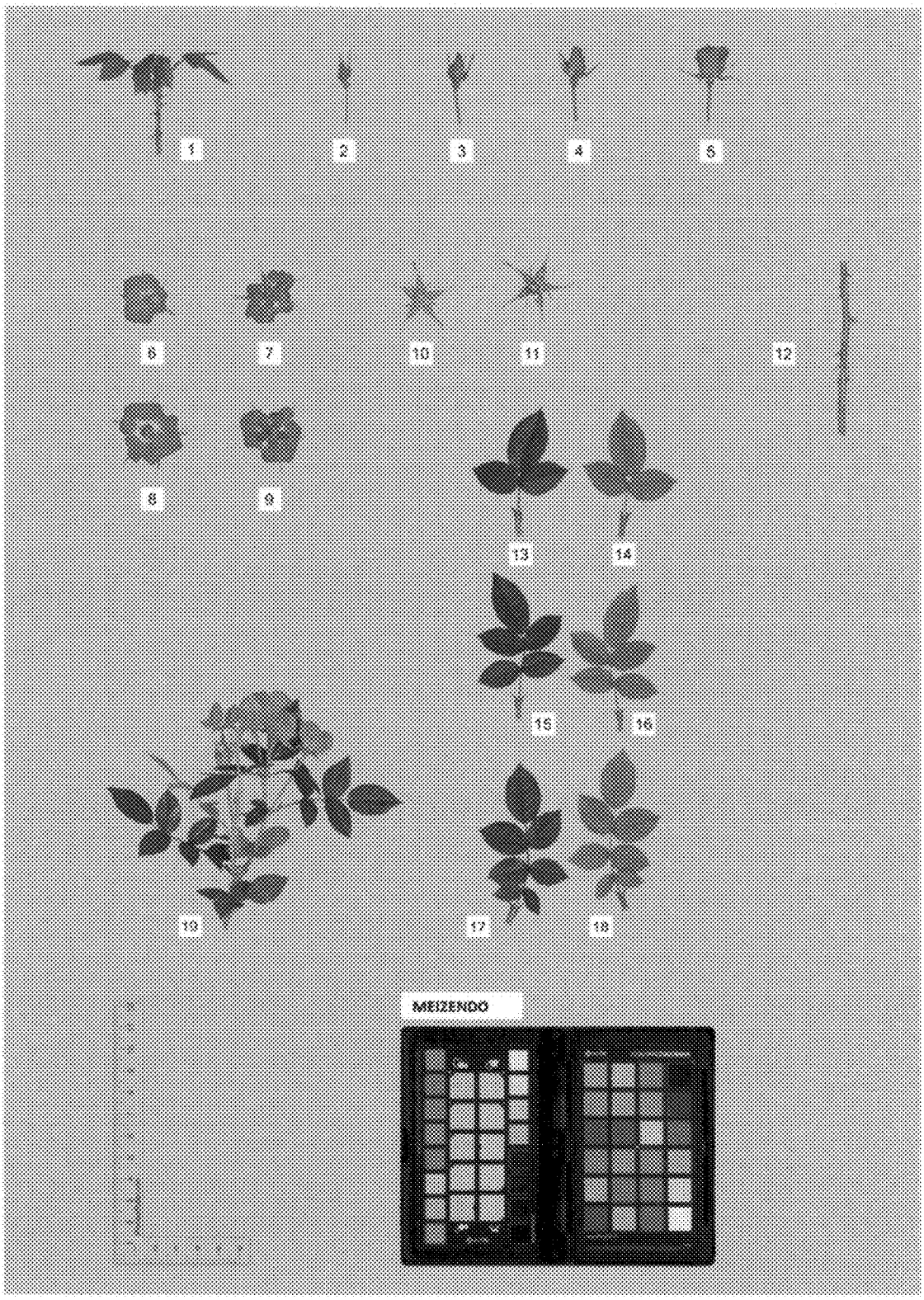
1
2
3
4
5
6
7
10
11
12
8
9
13
14
15
16
19
17
18
MEIZENDO